(12) United States Patent
Mayes et al.

(10) Patent No.: US 10,279,042 B2
(45) Date of Patent: **\*May 7, 2019**

(54) ONE-STEP PROCESSING OF HYDROGELS FOR MECHANICALLY ROBUST AND CHEMICALLY DESIRED FEATURES

(71) Applicant: Board of Regents, The University of Texas System, Austin, TX (US)

(72) Inventors: Sarah Mayes, Austin, TX (US); Christine Schmidt, Gainesville, FL (US)

(73) Assignee: Board of Regents, The University of Texas System, Austin, TX (US)

( * ) Notice: Subject to any disclaimer, the term of this patent is extended or adjusted under 35 U.S.C. 154(b) by 410 days.

This patent is subject to a terminal disclaimer.

(21) Appl. No.: 14/604,298

(22) Filed: Jan. 23, 2015

(65) Prior Publication Data

US 2015/0133377 A1 May 14, 2015

Related U.S. Application Data

(63) Continuation of application No. 13/269,366, filed on Oct. 7, 2011, now Pat. No. 8,946,194.

(60) Provisional application No. 61/391,410, filed on Oct. 8, 2010.

(51) Int. Cl.
| | |
|---|---|
| A61K 31/738 | (2006.01) |
| A61K 31/7008 | (2006.01) |
| A61K 31/734 | (2006.01) |
| A61K 31/728 | (2006.01) |
| A61K 47/36 | (2006.01) |

(52) U.S. Cl.
CPC ............ *A61K 47/36* (2013.01); *A61K 31/738* (2013.01)

(58) Field of Classification Search
CPC .............. A61K 31/738; A61K 31/7008; A61K 31/734; A61K 31/728
USPC .................................... 514/62, 53, 54; 536/3
See application file for complete search history.

(56) References Cited

U.S. PATENT DOCUMENTS

| | | |
|---|---|---|
| 4,141,973 A | 2/1979 | Balazs |
| 4,818,542 A | 4/1989 | Deluca |
| 4,937,270 A | 6/1990 | Hamilton |
| 5,017,229 A | 5/1991 | Burns |
| 5,531,716 A | 7/1996 | Luzio |
| 5,531,735 A | 7/1996 | Thompson |
| 5,563,186 A | 10/1996 | Thompson |
| 5,622,707 A | 4/1997 | Dorigatti |
| 5,714,166 A | 2/1998 | Tomalia |
| 5,750,585 A | 5/1998 | Park |
| 5,760,200 A | 6/1998 | Miller |
| 5,863,551 A | 1/1999 | Woerly |
| 5,919,442 A | 7/1999 | Yin |
| 5,939,323 A | 8/1999 | Valentini |
| 6,007,833 A | 12/1999 | Chudzik |
| 6,030,958 A | 2/2000 | Burns |
| 6,060,534 A | 5/2000 | Ronan |
| 6,096,018 A | 8/2000 | Luzio |
| 6,124,273 A | 9/2000 | Drohan |
| 6,133,325 A | 10/2000 | Schwartz |
| 6,156,572 A | 12/2000 | Bellamkonda |
| 6,174,999 B1 | 1/2001 | Miller |
| 6,184,266 B1 | 2/2001 | Ronan |
| 6,235,726 B1 | 5/2001 | Burns |
| 6,271,278 B1 | 8/2001 | Park |
| 6,294,202 B1 | 9/2001 | Burns |
| 6,334,968 B1 | 1/2002 | Shapiro |
| 6,368,356 B1 | 4/2002 | Zhong |
| 6,372,244 B1 | 4/2002 | Antanavich |
| 6,387,978 B2 | 5/2002 | Ronan |
| 6,410,044 B1 | 6/2002 | Chudzik |
| 6,425,918 B1 | 7/2002 | Shapiro |

(Continued)

FOREIGN PATENT DOCUMENTS

| | | |
|---|---|---|
| EP | 1806367 | 11/2007 |
| JP | 06100468 | 9/1992 |

(Continued)

OTHER PUBLICATIONS

Duffy, David C., et al., "Rapid Prototyping of Microfluidic Systems in Poly(dimethylsiloxane)" Analytical Chemistry, vol. 70, No. 23, Cambridge, Massachusetts, Dec. 1, 1998, pp. 4974-4984.
International Search Report and Written Opinion in PCT/US2011/055461, dated Dec. 1, 2011, 10 pages.
Lindenhayn, K. et al., "Retention of Hyaluronic Acid in Alginate Beads: Aspects for in vitro Cartilage Engineering," J. Biomed. Mater. Res., (1999), vol. 44, pp. 149-155.
Masters, Kristyn S., et al., "Designing Scaffolds for Valvular Interstitial Cells: Cell Adhesion and Function on Naturally Derived Materials," J. Biomed. Mater Res. 71A, (2004) pp. 172-180.
Miralles, G., et al., "Sodium Alginate Sponges With or Without Sodium Hyaluronate: In Vitro Engineering of Cartilage," J. Biomed. Mater Res., vol. 57, (2001), pp. 268-278.

(Continued)

*Primary Examiner* — Shaojia A Jiang
*Assistant Examiner* — Everett White
(74) *Attorney, Agent, or Firm* — Trop, Pruner & Hu, P.C.

(57) ABSTRACT

The application of a highly controlled, micron-sized, branched, porous architecture to enhance the handling properties and degradation rate of hydrogels is described in the instant invention. A previously described pattern created through one-step nucleated crystallization in a hydrogel film creates tunable mechanical properties and/or chemical stability for use in tissue engineering applications. The bulk mechanical properties and the degradation rate of the material can be tuned easily by the addition or subtraction of crystalline structure or by the addition and subtraction of backfill material, making this useful for a variety of applications. Relevant mechanical properties that can be tuned through the application of this unique porosity are moduli, elasticity, tensile strength, and compression strength. The method of the present invention can be applied to biopolymers and natural materials as well as synthetic materials.

21 Claims, 6 Drawing Sheets

(56) References Cited

U.S. PATENT DOCUMENTS

| | | |
|---|---|---|
| 6,500,777 B1 | 12/2002 | Wiseman |
| 6,511,650 B1 | 1/2003 | Eiselt |
| 6,521,223 B1 | 2/2003 | Calias |
| 6,548,081 B2 | 4/2003 | Sadozai |
| 6,566,345 B2 | 5/2003 | Miller |
| 6,599,526 B2 | 7/2003 | Dimitrijevich |
| 6,600,011 B2 | 7/2003 | McDonnell |
| 6,608,117 B1 | 8/2003 | Gvozdic |
| 6,610,669 B1 | 8/2003 | Calias |
| 6,630,167 B2 | 10/2003 | Zhang |
| 6,630,457 B1 | 10/2003 | Aeschlimann |
| 6,638,917 B1 | 10/2003 | Li |
| 6,642,363 B1 | 11/2003 | Mooney |
| 6,653,240 B2 | 11/2003 | Crawford |
| 6,653,420 B2 | 11/2003 | Domschke |
| 6,693,089 B1 | 2/2004 | Li |
| 6,703,041 B2 | 3/2004 | Burns |
| 6,723,709 B1 | 4/2004 | Pressato |
| 6,750,262 B1 | 6/2004 | Hahnle |
| 6,767,928 B1 | 7/2004 | Murphy |
| 6,793,675 B2 | 9/2004 | Shapiro |
| 6,818,018 B1 | 11/2004 | Sawhney |
| 6,841,153 B1 | 1/2005 | Chegini |
| 6,869,938 B1 | 3/2005 | Schwartz |
| 6,897,271 B1 | 5/2005 | Domschke |
| 6,913,765 B2 | 7/2005 | Li |
| 6,924,370 B2 | 8/2005 | Chudzik |
| 6,943,154 B2 | 9/2005 | Miller |
| 6,960,617 B2 | 11/2005 | Omidian |
| 6,991,652 B2 | 1/2006 | Burg |
| 7,022,313 B2 | 4/2006 | O'Connor |
| 7,083,697 B2 | 8/2006 | Dao |
| 7,201,917 B2 | 4/2007 | Malaviya |
| 7,235,295 B2 | 6/2007 | Laurencin |
| 7,347,988 B2 | 3/2008 | Hu |
| 7,459,021 B2 | 12/2008 | Bukshpan |
| 7,553,903 B2 | 6/2009 | Riegel |
| 7,572,894 B2 | 8/2009 | Jin |
| 7,629,388 B2 | 12/2009 | Mikos |
| 7,682,540 B2 | 3/2010 | Boyan |
| 7,741,476 B2 | 6/2010 | Lebreton |
| 7,758,654 B2 | 7/2010 | Hoganson |
| 7,919,542 B2 | 4/2011 | Hudgins |
| 7,968,110 B2 | 6/2011 | Hubbard |
| 7,988,992 B2 | 8/2011 | Omidian |
| 7,989,505 B2 | 8/2011 | Hu |
| 7,998,380 B2 | 8/2011 | Turng |
| 8,025,901 B2 | 9/2011 | Kao |
| 8,110,242 B2 | 2/2012 | Hawkins |
| 8,133,840 B2 | 3/2012 | Mika |
| 8,323,675 B2 | 12/2012 | Greenawalt |
| 8,946,194 B2 * | 2/2015 | Mayes ............ 514/53 |
| 2002/0131933 A1 | 9/2002 | Delmotte |
| 2003/0134132 A1 | 7/2003 | Winterton |
| 2004/0138329 A1 | 7/2004 | Hubbell |
| 2005/0107868 A1 | 5/2005 | Nakayama |
| 2007/0031498 A1 | 2/2007 | Zong |
| 2007/0202084 A1 | 8/2007 | Sadozai |
| 2008/0069257 A1 | 3/2008 | Yeo |
| 2008/0182012 A1 | 7/2008 | Fisher |
| 2008/0264793 A1 | 10/2008 | Vigh |
| 2008/0292664 A1 | 11/2008 | Giammona |
| 2009/0062233 A1 | 3/2009 | Ji |
| 2009/0081265 A1 | 3/2009 | Peppas |
| 2009/0170973 A1 | 7/2009 | Mattiasson |
| 2010/0062232 A1 | 3/2010 | Schauer |
| 2010/0273667 A1 | 10/2010 | Kotov |
| 2011/0008442 A1 | 1/2011 | Zawko |
| 2012/0039959 A1 | 2/2012 | Tessmar |
| 2012/0282302 A1 | 11/2012 | McCanless |

FOREIGN PATENT DOCUMENTS

| | | |
|---|---|---|
| JP | 04235124 | 5/1995 |
| JP | 2003062057 | 8/2001 |
| JP | 2001212224 | 12/2001 |
| KR | 20020027747 | 4/2002 |
| KR | 20020032351 | 5/2002 |
| KR | 20030055102 | 7/2003 |
| WO | 9739737 | 10/1997 |
| WO | 2002092678 | 11/2002 |
| WO | 2005020849 | 10/2005 |
| WO | 2009108760 | 9/2009 |

OTHER PUBLICATIONS

Zawko, Scott A., et al., "Crystal Templating Dendritic Port Networks and Fibrillar Microstructure into Hydrogels," Acta Biomaterials, vol. 6, (2010), pp. 2415-2421.

Huang, Jen-Huang, et al., "Rapid Fabrication of Bio-inspired 3D Microfluidic Vascular Networks," Advanced Materials, vol. 21, WILEY-VCH, Weinheim, Jul. 10, 2009, p. 3567.

Depierro, Michael A., et al., "Influence of Polymerization Conditions on Nanostructure and Properties of Polyacrylamide Hydrogels Templated from Lyotropic Liquid Crystals," Chemical Materials, vol. 18, No. 23, American Chemical Society, Iowa City, Iowa, Oct. 18, 2006, pp. 5609-5617.

Huang, Jen-Huang, et al., "Rapid Fabrication of 3-D Branched Microvascular Flow Networks," Twelfth International Conference on Miniaturized Systems for Chemistry and Life Sciences, San Diego, California, Oct. 12-16, 2008, pp. 1435-1437.

Seidel, Juliana Matos, et al., "Synthesis of PolyHEMA Hydrogels for Using as Biomaterials. Bulk and Solution Radical-Initiated Polymerization Techniques," Materials Research, vol. 3, No. 3, Jul. 2000, 8 pages.

Cho, W. J., et al., "Alginate Film as a Novel Post Surgical Tissue Adhesion Barrier," Journal of Biomaterials, Science-Polymer Edition, 21 (6-7), 2010, pp. 701-713.

Bekkers, John M., et al., "Targeted Dendrotomy Reveals Active and Passive Contributions of the Dendritic Tree to Synaptic Integration and Neuronal Output," PNAS, vol. 104, No. 27, Jul. 3, 2007, pp. 11447-11452.

Brisken, Catherin, et al., "Alveolar and Lactogenic Differentiation," J. Mammary Gland Biol. Neoplasia, (2006), 11: pp. 239-248.

Chung, Cindy, et al., "Effects of Auricular Chondrocyte Expansion on Neocartilage Formation in Photocrosslinked Hyaluronic Acid Networks," Tissue Eng., Sep. 2006, 12(9): pp. 2665-2673.

International Search Report and Written Opinion in PCT/US2009/035257, dated Oct. 12, 2009, 12 pages.

Khademhosseini, Ali, et al., "Microscale Technologies for Tissue Engineering and Biology," PNAS, vol. 103, No. 8, Feb. 21, 2006, pp. 2480-2487.

King, Kevin R., et al., "Biodegradable Microfluidics," Adv. Mater, vol. 16, No. 16, Nov. 18, 2004, pp. 2007-2012.

Larina, Olga, et al., "Ca2+ Dynamics in Salivary Acinar Cells: Distinct Morphology of the Acinar Lumen Underlies Near-Synchronous Global Ca2+ Responses," Journal of Cell Science, 118: pp. 4131-4139.

Leach, Jennie Baier, et al., "Photocrosslinked Hyaluronic Acid Hydrogels: Natural, Biodegradable Tissue Engineering Scaffolds," Biotechnol. Bioeng. 82: pp. 578-259.

Ma, Peter X., et al., "Biodegradable polymer Scaffolds with Well-Defined Interconnected Spherical Pore Network," Tissue Engineering, vol. 7, No. 1, (2001), pp. 22-39.

Oaki, Yuya, et al., "Experimental Demonstration for the Morphological Evolution of Crystals Grown in Gel Media," Crystal Growth & Design, vol. 3, No. 5, Jun. 27, 2003, pp. 711-716.

Peppas, N.A., et al., "Hydrogels in Pharmaceutical Formulations," European Journal of Pharmaceutics and Biopharmaceutics, (2000), 50, pp. 27-46.

Shah, Mita M., et al., "Branching Morphogenesis and Kidney Disease," Development 131, (2004) pp. 1449-1462.

Tsang, Valerie Liu, et al., "Fabrication of 3D Hepatic Tissues by Additive Photopatterning of Cellular Hydrogels," The FASEB Journal, 21, (2007), pp. 790-801.

Uludag, Hasan, et al., "Technology of Mammalian Cell Encapsulation," Advanced Drug Delivery Reviews, (2000), 42: pp. 29-64.

(56) References Cited

OTHER PUBLICATIONS

Xu, An-Wu, et al., "Biomimetic Mineralization," J. Mater. Chem., (2007), 17, pp. 415-449.
Yang, Shoufeng, et al., "The Design of Scaffolds of Use in Tissue Engineering. Part II. Rapid Prototyping Techniques," Tissue Engineering, vol. 8, No. 1, (2002), 11 pages.
Oerther, S., et al., "Hyaluronate-Alginate Gel As A Novel Biomaterial: Mechanical Properties and Formation Mechanism," Biotechnology Bioeng., 63, 1999, pp. 2006-2215.
Oerther, S., et al., "High Interaction Alginate-Hyaluronate Association by Hyaluronate Deacetylation for The Preparation of Efficient Biomaterials," Biopolymers, 54, 2000, pp. 273-281.
U.S. Appl. No. 12/919,667, filed Aug. 26, 2010, entitled "Dendritic Macroporous Hydrogels Prepared by Crystal Templating," by Scott Zawko.
U.S. Appl. No. 13/269,344, filed Oct. 7, 2011, entitled "Anti-Adhesive Barrier Membrane Using Alginate and Hyaluronic Acid for Biomedical Application," by Sarah Mayes.
U.S. Patent and Trademark Office, Office Action dated Jun. 25, 2013 in U.S. Appl. No. 13/269,344, ("Schmidt") (pp. 7-8 describing how Schmidt includes a hydrogel having hyaluronic acid and crosslinked alginate).

\* cited by examiner

ONE-STEP PROCESSING OF HYDROGELS FOR MECHANICALLY ROBUST AND CHEMICALLY DESIRED FEATURES

CROSS-REFERENCE TO RELATED APPLICATION

This application is a continuation of U.S. Utility patent application Ser. No. 13/269,366 filed on Oct. 7, 2011 and entitled "One-Step Processing of Hydrogels for Mechanically Robust and Chemically Desired Features," which claims priority to U.S. Provisional Patent Application No. 61/391,410 filed on Oct. 8, 2010 and entitled "One-Step Processing of Hydrogels for Mechanically Robust and Chemically Desired Features." The content of each of the above applications is hereby incorporated by reference.

STATEMENT OF FEDERALLY FUNDED RESEARCH

This invention was made with government support under Grant no. BES0201744 and BES0500969 awarded by the National Science Foundation. The government has certain rights in this invention.

TECHNICAL FIELD OF THE INVENTION

The present invention relates in general to the field of biopolymers and hydrogels, and more particularly to enhancing the handling properties and degradation rate of hydrogels by creating highly controlled micron-sized porosity in a one-step process.

INCORPORATION-BY-REFERENCE OF MATERIALS FILED ON COMPACT DISC

None.

REFERENCE TO A SEQUENCE LISTING

None.

BACKGROUND OF THE INVENTION

Without limiting the scope of the invention, its background is described in connection with methods of enhancing mechanical and degradation properties of hydrogels and biopolymers.

WIPO Patent Publication No. WO 2009/108760 A8 (Zawko and Schmidt, 2009) discloses a hydrogel and a method of making a porous hydrogel by preparing an aqueous mixture of an uncrosslinked polymer and a crystallizable molecule; casting the mixture into a vessel; allowing the cast mixture to dry to form an amorphous hydrogel film; seeding the cast mixture with a seed crystal of the crystallizable molecule; growing the crystallizable molecule into a crystal structure within the uncrosslinked polymer; crosslinking the polymer around the crystal structure under conditions in which the crystal structure within the crosslinked polymer is maintained; and dissolving the crystals within the crosslinked polymer to form the porous hydrogel.

SUMMARY OF THE INVENTION

The present invention discloses the application of a highly controlled, micron-sized, branched, porous architecture to enhance the handling properties and degradation rate of hydrogels by a simple one-step process involving the addition or subtraction of crystalline structure or by the addition and subtraction of backfill material. This method of creating pores works with natural biopolymers such as hyaluronic acid and alginate. The features of the pores are very fine and intricate and cannot be made by any other technique. The crystal-templated hydrogels of the present invention can be used as materials for tissue engineering devices. The pores resemble the fine, intricate branching patterns found in natural tissues such as microvasculature and neuronal outgrowth. These hydrogels can guide the infiltration of cells, neurite outgrowth, and vascularization into biomimetic patterns.

In one embodiment the instant invention discloses a method of making a directed branched porous polymer comprising the steps of: i) preparing an aqueous mixture of one or more uncrosslinked polymers and a crystallizable molecule, ii) casting the aqueous mixture onto a vessel, a slide, a plate, tissue-culture dish or combinations and modifications thereof to form a cast mixture, iii) drying the cast mixture to form an amorphous polymer film, iv) seeding the cast mixture with a seed crystal of the crystallizable molecule, v) growing the crystallizable molecule into a crystal structure within the uncrosslinked polymer, vi) exposing the cast mixture to ultraviolet light, wherein the exposure results in a gelling or a crosslinking of the polymer, vii) crosslinking the uncrosslinked polymer around the crystal structure by an addition of one or more crosslinking agents under conditions in which the crystal structure within the crosslinked polymer is maintained, viii) removing the one or more crystals of the crystallizable polymers by rinsing with water to form a branched porous polymer base film, ix) removing water from the porous polymer base film by controlled dessication under pressure, and x) diffusing one or more backfill materials into the one or more pores of the branched porous polymer, wherein the backfill materials can be same or different from the polymer base film material.

In one aspect the method comprises the additional step of simultaneously or separately crosslinking or covalently binding the backfill materials to itself or the branched porous polymer forming base film material. In another aspect the method comprises the optional step of forming a crosslink between the branched porous polymer base film material and the backfill material in the one or more pores of the branched porous polymer, wherein the base film materials and the backfill materials are different. In yet another aspect the directed branched porous polymer is a hydrogel, a film, a barrier or combinations and modifications thereof. In another aspect the polymer comprises nucleic acids, amino acids, saccharides, lipids and combinations thereof, in monomeric, dimeric, trimeric, oligomeric, multimeric or polymeric forms. In another aspect the polymer is selected from the group consisting of collagen, chitosan, gelatin, pectins, alginate, hyaluronic acid, heparin, and mixtures thereof.

In one aspect of the method disclosed hereinabove the one or more backfill materials comprise polymers, small molecules, drugs, hormones, proteins or combinations and modifications thereof. In another aspect the crystallizable molecule comprises a small organic molecule selected from a salt, urea, beta cyclodextrin, glycine, and guanidine. In another aspect an addition or a subtraction of the one or more backfill materials modify one or more bulk mechanical properties and a degradation rate of the branched porous polymer. In yet another aspect the mechanical properties are selected from the group consisting of moduli, elasticity, tensile strength, and compression strength. In another aspect the polymer is gelled by a chemical crosslink, a physical crosslink or a combination; wherein said crosslink is induced by an UV method, a temperature method, a pH method, an ion or ion-radical based method or combinations thereof. In one aspect the polymer comprises a biopolymer that maybe a synthetic or a non-synthetic polymer and is biodegradable, biocompatible, and hydrophilic.

In one aspect the aqueous mixture comprises alginate and hyaluronic acid. In a specific aspect the crystallizable molecule comprises urea and the backfill material is hyaluronic acid. In another aspect the crosslinking agent selected from group consisting of calcium chloride, p-Azidobenzoyl hydrazide, N-5-Azido-2-nitrobenzoyloxsuccinimide, disuccinimidyl glutamate, dimethyl pimelimidate-(2)HCl, dimethyl suberimidate-2 HCl, disuccinimidyl suberate, bis[sulfosuccinimidyl suberate], 1-ethyl-3-[3-dimethylaminopropyl]carbodiimide-HCl, isocyanate, aldehyde, glutaraldehyde, paraformaldehyde, and derivatives thereof. In yet another aspect the method comprises the optional step of encapsulation one or more agents selected from drugs, growth factors, hormones, proteins or combinations thereof in the one or more pores or the matrix of the branched porous polymer.

Another embodiment of the instant invention relates to a directed branched porous polymer made by a method that comprises: i) preparing an aqueous mixture of one or more uncrosslinked polymers and a crystallizable molecule, ii) casting the aqueous mixture onto a vessel, a slide, a plate, tissue-culture dish or combinations and modifications thereof to form a cast mixture, iii) drying the cast mixture to form an amorphous polymer film, iv) seeding the cast mixture with a seed crystal of the crystallizable molecule, v) growing the crystallizable molecule into a crystal structure within the uncrosslinked polymer, vi) exposing the cast mixture to ultraviolet light, wherein the exposure results in a gelling or a crosslinking of the polymer, vii) crosslinking the uncrosslinked polymer around the crystal structure by an addition of one or more crosslinking agents under conditions in which the crystal structure within the crosslinked polymer is maintained, viii) removing the one or more crystals of the crystallizable polymers by rinsing with water to form a branched porous polymer base film, ix) removing water from the base film by controlled dessication under pressure, and x) diffusing one or more backfill materials into the one or more pores of the branched porous polymer, wherein the backfill materials can be same or different from the porous polymer base film material.

In one aspect of the method above comprises the additional step of simultaneously or separately crosslinking or covalently binding the backfill materials to itself or the porous polymer forming base film material. In another aspect the method comprises the optional step of forming a crosslink between the porous polymer base film material and the backfill material in the one or more pores of the porous polymer, wherein the base film materials and the backfill materials are different. In yet another aspect the directed branched porous polymer is a hydrogel, a film, a barrier or combinations and modifications thereof. In another aspect the polymer comprises nucleic acids, amino acids, saccharides, lipids and combinations thereof, in monomeric, dimeric, trimeric, oligomeric, multimeric or polymeric forms. In another aspect the polymer is selected from the group consisting of collagen, chitosan, gelatin, pectins, alginate, hyaluronic acid, heparin, and mixtures thereof.

In yet another aspect the one or more backfill materials comprise polymers, small molecules, drugs, hormones, proteins or combinations and modifications thereof. In one aspect the crystallizable molecule comprises a small organic molecule selected from a salt, urea, beta cyclodextrin, glycine, and guanidine. In another aspect an addition or a subtraction of the one or more backfill materials modify one or more bulk mechanical properties (selected from the group consisting of moduli, elasticity, tensile strength, and compression strength) and a degradation rate of the branched porous polymer. In another aspect the polymer is gelled by a chemical crosslink, a physical crosslink or a combination; wherein said crosslink is induced by an UV method, a temperature method, a pH method, an ion or ion-radical based method or combinations thereof. In a specific aspect the polymer comprises a synthetic or non-synthetic biopolymer that is non-cytotoxic, biodegradable, biocompatible, and hydrophilic. In other related aspects the aqueous mixture comprises alginate and hyaluronic acid, the crystallizable molecule comprises urea, and the backfill material is hyaluronic acid.

In another aspect the crosslinking agent selected from group consisting of calcium chloride, p-Azidobenzoyl hydrazide, N-5-Azido-2-nitrobenzoyloxsuccinimide, disuccinimidyl glutamate, dimethyl pimelimidate-(2)HCl, dimethyl suberimidate-2 HCl, disuccinimidyl suberate, bis[sulfosuccinimidyl suberate], 1-ethyl-3-[3-dimethylaminopropyl]carbodiimide-HCl, isocyanate, aldehyde, glutaraldehyde, paraformaldehyde, and derivatives thereof. In another aspect the method comprises the optional step of encapsulating one or more agents selected from drugs, growth factors, hormones, proteins or combinations thereof in the one or more pores or the matrix of the porous polymer. In yet another aspect the branched porous polymer prevents tissue adhesion following surgery, acts a tissue scaffold, promotes wound healing, delivers drug or growth factors to the support healing, inhibits or prevents infiltration of blood, blood protein, fibroblasts, and inflammatory responses in the surgical site.

In yet another embodiment the instant invention relates to a method of making a porous hydrogel comprising the steps of: preparing an aqueous mixture comprising hyaluronic acid, alginic acid, and urea, casting the aqueous mixture onto a vessel, a slide, a plate, tissue-culture dish or combinations and modifications thereof to form a cast mixture, drying the cast mixture to form an amorphous hydrogel film, seeding the cast mixture with one or more urea crystals, growing the urea into a crystal structure within the uncrosslinked alginate, exposing the cast mixture to ultraviolet light, wherein the exposure results in a gelling or a crosslinking of the alginate, crosslinking the uncrosslinked alginate around the urea crystal structure by an addition of calcium chloride under conditions in which the urea crystal structure within the crosslinked alginate is maintained, removing the one or more urea crystals by rinsing with water to form the porous hydrogel base film, removing water from the base film by controlled dessication under pressure, and diffusing hyaluronic acid into the one or more pores of the hydrogel.

In one aspect of the method described hereinabove the method comprises the optional step of encapsulating one or more agents selected from drugs, growth factors, hormones, proteins or combinations thereof in the one or more pores or the matrix of the porous hydrogel. In another aspect the hydrogel prevents tissue adhesion following surgery, acts a tissue scaffold, promotes wound healing, delivers drug or growth factors to the support healing, inhibits or prevents infiltration of blood, blood protein, fibroblasts, and inflammatory responses in the surgical site. In yet another aspect an addition or a subtraction of the one or more backfill materials modify one or more bulk mechanical properties and a degradation rate of the porous hydrogel. More specifically, the mechanical properties are selected from the group consisting of moduli, elasticity, tensile strength, and compression strength.

BRIEF DESCRIPTION OF THE DRAWINGS

For a more complete understanding of the features and advantages of the present invention, reference is now made to the detailed description of the invention along with the accompanying figures and in which:

FIGS. 2A-2D show the surface modification of templated alginate films.

FIGS. 4A and 4B show the ASTM D638 tensile testing of.

FIGS. 5A and 5B are examples of alginate/HA ureatemplated films.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The instant invention describes the application of a highly controlled, micron-sized, branched, porous architecture to enhance the handling properties and degradation rate (either surface or bulk degradation), of hydrogels. A previously described pattern created through one-step nucleated crystallization in a hydrogel film creates tunable mechanical properties and/or chemical stability for use in tissue engineering applications. The simplicity of the process of the present invention is that bulk mechanical properties and the degradation rate of the material can be tuned easily by the addition or subtraction of crystalline structure or by the addition and subtraction of backfill material, making this useful for a variety of applications.

Relevant mechanical properties that can be tuned through the application of this unique porosity are moduli, elasticity, tensile strength, and compression strength. Processed hydrogels can hold a suture, be cut or be manipulated with surgical tools even when hydrated with biological fluids, and be rolled, squeezed, stretched, bent, folded or crumpled without compromising original shape. Hydrogels can be synthesized very thin to sponge bulk on the order of 30 microns to 2 millimeters. The method of the present invention can be applied to biopolymers and natural materials as well as synthetic materials.

The unique porous architecture may be backfilled by diffusion of material into the preserved, hierarchical porosity. Backfilled material is simultaneously or separately, crosslinked or covalently bound to itself and/or base film, maintaining the desired pattern. The complex, multiple-material construct may contain polymers/materials of different chi parameters, creating a phase-separated film with further tunable handling properties and degradation rate. The backfilled material may also contain small molecules available for growth factor release or drug release and could be used as materials for tissue engineering devices.

The hydrogel base material may also be degraded, leaving the hierarchically branched, crosslinked backfilled material as a scaffold or strengthening complex. The unique features of the invention are: i) a highly controlled, micron-sized porosity created in one step, can finely modulate the mechanical properties and degradation rate of hydrogels, ii) mechanical properties such as moduli, elasticity, tensile strength, and compression strength can be highly controlled into desired ranges, and iii) chemically desired crosslinks can be facilitated in one step by backfilling pores with another material.

The unique benefits are: i) the resulting hydrogel(s) can be manipulated in a surgically relevant manner and, subsequently, return or retain original shape, ii) this method works with biopolymers, iii) the resulting hydrogel(s) can persist throughout the appropriate duration for given use, and iv) the mechanical and/or chemical modulation may occur in one step. No other technology has this combination of features.

There are no existing methods in literature that are similar to the technique of the present invention. Currently employed methods to modulate mechanical and degradation properties in tissue engineering scaffolds are described herein below.

The most common current methods are increasing/decreasing crosslinking, blending, hydrogen bond creation, and colloidal particle addition. Very common to tissue engineering materials, crosslinking provides controllable covalent bonding shown to be directly proportional to mechanical integrity, with greater crosslinking being associated with higher strength. The advantage to this method is that no additional materials are required as a strengthening agent (as in a mesh or fibrous network). The disadvantage to this method is that increased crosslinking often leads to brittle structures and so other methods are required to provide elasticity and/or plastic deformation. Also increased crosslinking requires more crosslinking agents, which are often toxic.

Blending techniques are usually straightforward in that another material is added to the base material for the purpose of strengthening. Colloidal particle addition requires the introduction of a suspended material in the surface or bulk of the base material. These particles act as fillers or bulking agents. While these methods are straightforward, there may be advantages to being able to strengthen without additional materials. Also, blending can be non-isotropic or cause unwanted gradients or clumps, and does not lend itself to finely tuning.

Hydrogen bonds are very strong, creating significant changes in mechanical strength and degradation rates. Some techniques allow for specific hydrogen bond formation with fine tuning capability but require many steps and specific equipment. Other techniques are simplified without fine-tuning capabilities.

It is well known in tissue engineering that mechanical properties of scaffolds and implants directly influence cellular response, differentiation, proliferation, and signaling. Finely tuning the mechanical properties of biopolymers and hydrogels has proven to be a difficult task without the use of lasers, additional support materials or sophisticated cross-linking methods such as direct-write, lithography or micro-fabrication. The invention presented hereinabove provides a simple, one-step tuning method to significantly alter the mechanical properties of biopolymers or synthetic hydrogels. Furthermore, it is difficult to simultaneously produce a tunable degradation rate. The present invention may also be utilized to tune the degradation rate of the hydrogel construct.

Post-surgical adhesions tether tissues that should remain separate. Adhesions result from impaired autologous natural immune response. Surgical adhesions continue to plague the recovery period, with current technologies falling short of adhesion prevention. Incidence of adhesions following surgery is 80% (Yeo, 2007) resulting in chronic pain, limited motion, organ dysfunction, and even death (Cui et al, 2009). The healthcare costs associated with this are over $3.45 billion, annually (Wiseman, et al., 2010). Current approaches for preventing adhesions include better surgical practices (Holmdahl et al., 1997) (for e.g., powder free gloves, laparoscopic procedures, and reduction of dessication), biocompatible barrier devices (for e.g., polymer solutions, in situ crosslinkable hydrogels, pre-formed membranes), and pharmacotherapy agents like steroidal anti-inflammatory drugs (Dexamethasone; progesterone; hydrocortisone; prednisone), non-steroidal anti-inflammatory drugs (Ibuprofen; flurbiprofen; indomethacin; tolmetin; nimesulide), inhibitors of proinflammatory cytokines (Antibodies to transforming growth factor (TGF)-b1), antihistamine (Diphenhydramine; promethazine), free radical scavengers (Melatonin; vitamin E; superoxide dismutase), Anticoagulants (heparin), proteolytic agents (tissue-type plasminogen activator; streptokinase; urokinase; pepsin; trypsin; Neurokinin 1 receptor antagonist), and antiproliferative agents (mitomycin).

The most effective anti-adhesion barrier on the market reduces adhesion formation by only 50%. Many products are based on synthetic materials because of superior handling capabilities and low manufacturing costs. However, these synthetic materials are rendered ineffective in the presence of blood or blood proteins. The invention presented herein addresses the problems listed above and provides an effective method of blocking the infiltration of unwanted inflammatory response while maintaining robust mechanical properties for surgical handling. Because the present invention is constructed of natural materials, the risk of further aggravation is minimized, while blood and blood proteins will not adhere. Barriers on the market made from natural materials also degrade too quickly, allowing for adhesion formation. The present technology has a tunable degradation rate so that the barrier persists during the healing process.

Current products on the market that are most effective have poor handling properties. They are brittle when dry and are rendered inapplicable when wet. In an OR environment, a suitable solution would be able to maintain mechanical integrity when wet. The present invention offers superior handling properties when wet including in vivo repositioning capabilities and suturability.

The present invention describes the development of composite, dual-functioning materials to be placed at the interface between healing tissues and the surrounding tissues. The invention improves upon anti-adhesive biomaterial barriers, to aid in wound healing, and to modulate the inflammatory response. The present inventors have developed and characterize anti-adhesive hyaluronic acid HA-based material (biocompatible, non-immunogenic, non cell-adhesive, inhibits protein absorption, mechanically stable, cost effective, clinically sized, and appropriate degradation rate). In addition the present inventors have developed a bilayer biofunctionalized HA-based film that is biocompatible, bioabsorbable, non-immunogenic, dual functioning, regenerative, anti-adhesive, mechanically stable, cost effective, and clinically sized. Finally, they develop an injectable solution version of anti-adhesive film that is biocompatible, effective at reducing adhesions, encapsulates ibuprofen or tranexamic acid and has tunable release rates.

Hydrogels are generally polymer chain networks that are water-insoluble, but that absorb water. Often described as being "superabsorbent," hydrogels are able to retain up to 99% water and can be made from natural or synthetic polymers. Often, hydrogels will have a high degree of flexibility due to their high water content. Common uses for hydrogels include: sustained drug release, as scaffolds (e.g., in tissue engineering), as a thickening agent, as a biocompatible polymer, in biosensors and electrodes and for tissue replacement applications. Natural hydrogels may be made from agarose, methylcellulose, hyaluronic acid (HA), and other naturally-derived polymers.

HA is a linear polysaccharide with repeating disaccharide units composed of sodium D-glucuronate and N-acetyl-D-glucosamine. This naturally occurring glycosaminoglycan is a component of skin, synovial fluid, and subcutaneous and interstitial tissues. HA is metabolically eliminated from the body, and plays a role in protecting and lubricating cells and maintaining the structural integrity of tissues. Anionic carboxylic groups immobilize water molecules giving HA its viscoelastic and anti cell-adhesive properties. HA has been used in a variety of material designs for the prevention of postsurgical tissue adhesion. HA has been used as a dilute solution, a crosslinked hydrogel or combined with CMC into sheets. HA is biocompatible, bioabsorbable/non-immunogenic (non-animal), very non-cell adhesive, polyanionic, hydrophilic, antifibrotic (1% HMW HA, Massie, 2005), pro-angiogenic and has been shown to reduce adhesion formation in animals and humans (Zawaneh, 2008; Diamond, 2006; Wiseman, 2010; Rajab, 2010). HA is clinically used to reduce adhesions: Seprafilm®, most effective and widely used anti-adhesion barrier on the market.

Alginic acid is biocompatible, bioabsorbable/non-immunogenic (non-animal) (Skjak-Braek, 1992), very non-cell adhesive, polyanionic, hydrophilic, cost effective, abundant (brown seaweed), mechanically viable for handling/suturing in ionically crosslinked form, and is shown to be significantly effective at adhesion prevention in animal models (Namba, 2006; Cho, 2010a; Cho, 2010b).

Attributes of alginate that statistically alter mechanical properties: (i) grade (Purification), (ii) gulcuronate to mannuronate ratio (High M ratio is pond-grown, primarily leaves, High G is deep sea harvested, primarily stems), and (iii) molecular weight/viscosity. However, highly purified alginate is very expensive ~$100/g, lower grade (inexpensive) alginates are not tested for molecular weight or G:M ratio, and purification processes are not standardized.

Figure 1:
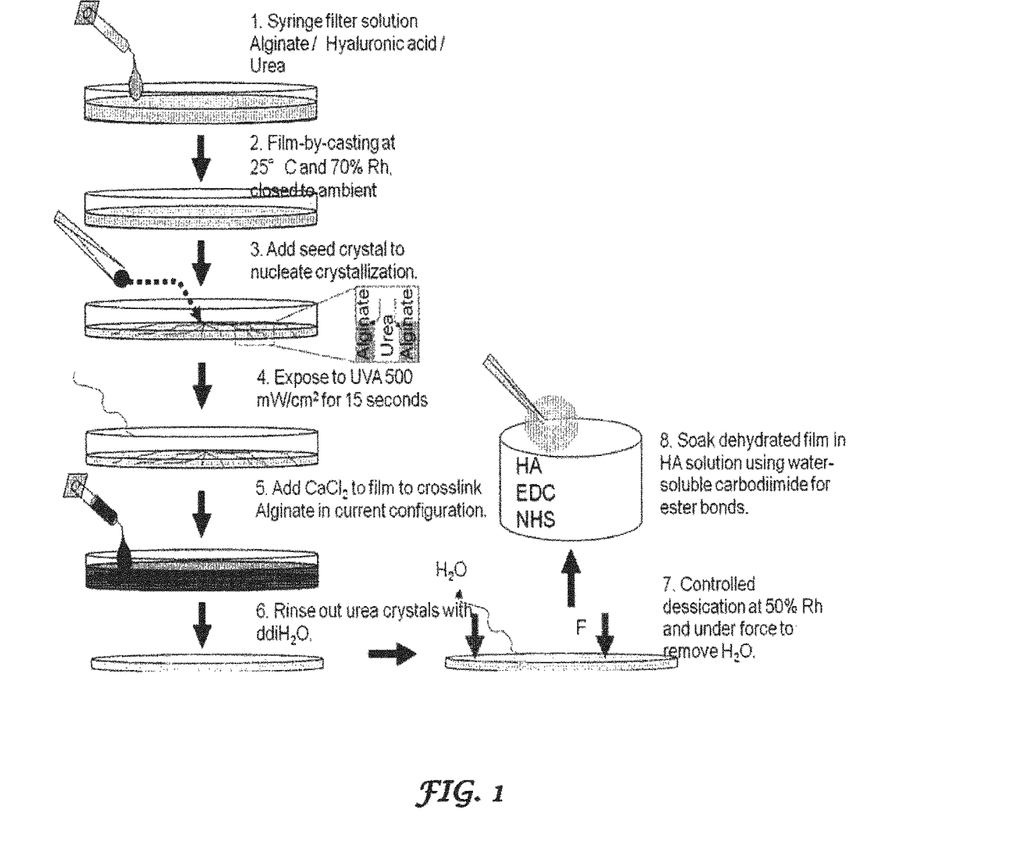
FIG. 1 is a schematic showing the techniques for fabricating the crystal-templated biopolymer hydrogels of the present invention.

Crystal templated hydrogels of alginate and HA were created by casting a droplet of solution containing a photocrosslinkable derivative of HA, a photocrosslinkable derivative of alginate with photoinitiator (PI) and urea (FIG. 1). The solvent is evaporated and a urea seed crystal is touched to the droplet to nucleate urea crystallization. After crystallization the alginate and HA are photocrosslinked by UV exposure. Alginate may be further crosslinked ionically and rinsed with water to remove the urea leaving behind an alginate/HA hydrogel templated with the pattern of the urea crystals. The hydrogel may then be dehydrated for further surface modification using crosslinking agents (such as water soluble carbodiimides in ethanol/deionized water mixtures).

The method for preparing the alginate/HA films as described in the present invention includes five steps: film casting, solvent evaporation, crystal growth, crosslinking, and rinsing. In the first step a syringe filter introduces a solution comprising alginate/GMHA/urea on a plate. The solution is then cast as a film at 25° C. at 70% relative humidity. Solvent evaporation is required to achieve the super-saturation conditions necessary for crystallization. Evaporation also greatly increases the biopolymer concentration and solution viscosity. The combination of high viscosity and hydrogen bonding suppresses spontaneous urea crystallization and facilitates super-saturation. Urea seed crystals are deposited on the tips of a fine pair of tweezers and is added to nucleate crystallization followed by exposure to UVA ($500$ mW/cm$^2$) for 15 secs. Crystal growth began immediately and produced long dendritic branches that extended from the center to the edge of the film. Within seconds the entire volume of the hydrogel films were filled with urea crystals. These crystals comprised the urea crystal template. The films may optionally be crosslinked by an addition of one or more cross linking agents (for example an ionic crosslinking solution like CaCl$_2$ is added to the film to crosslink the alginate). The urea crystals are then rinsed out with double distilled water. The film formed thus is subjected to controlled dessication under force to remove water at 50% relative humidity. The dehydrated film may be subjected to further surface modification by creating one or more ester or less hydrolysable bonds by a variety of techniques (e.g., soaking in a HA solution using water soluble carbodiimide for ester bonds).

Alginate films alone degraded too quickly in chelating environment. Calcium ions chelated by multiple salts and can degrade within a few hours. (Islam, 2010). Adding GMHA decreases degradation, but without compromising the mechanical strength provided by alginate. Alginate film, alone, is too brittle and breaks with little manipulation. Adding urea introduces micron-sized pores which provide flexibility because spaces accept forces first.

Figure 2A:
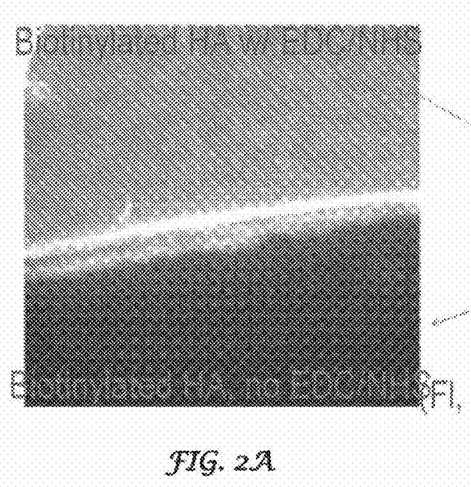
FIG. 2A fluorescent biotinylated HA crosslinked to surface labeled with FITC/Neutravadin. When not crosslinked, biotinylated HA washed away (4×)
Figure 2B:
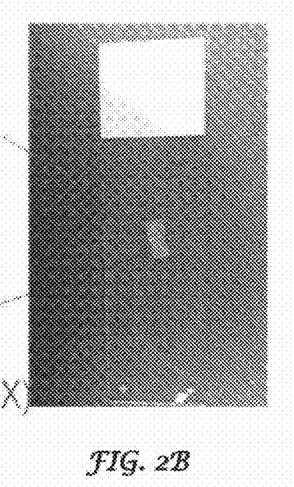
FIG. 2B is a glass slide for FIG. 2A.
Figure 2C:
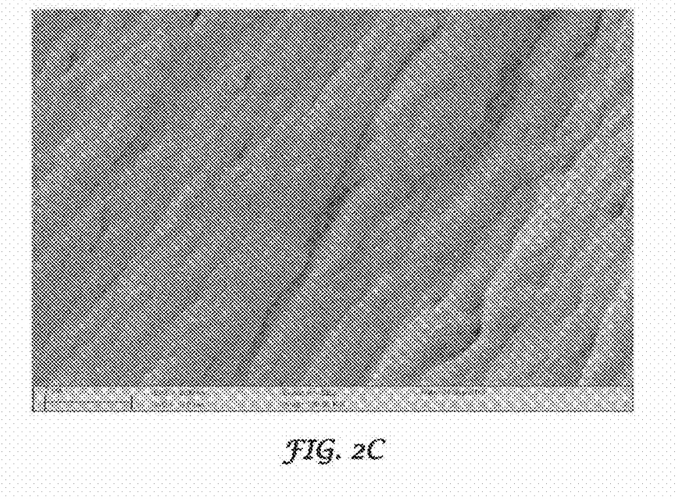
FIG. 2C is a SEM of the surface-modified film cross-sectional surface indicating pores filled, scale bar 2 μm.
Figure 2D:
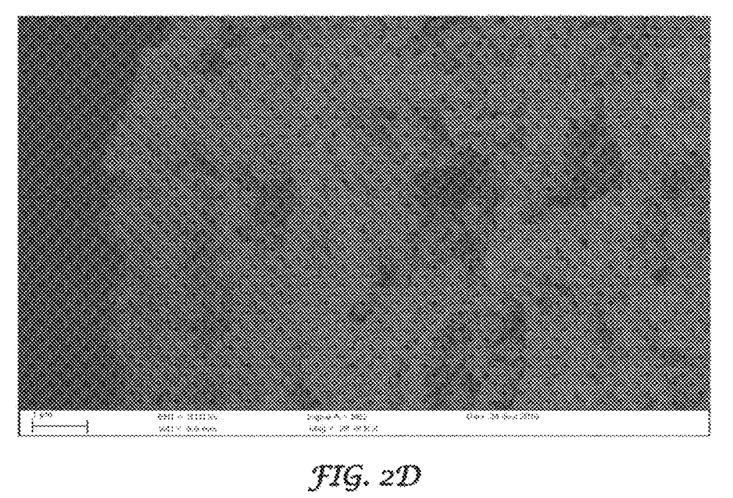
FIG. 2D is a SEM of a templated film, no surface modification, cross-sectional surface indicating unfilled porous, scale bar 1 μm.

FIGS. 2A-2D show the surface modification of templated alginate films. FIG. 2A shows fluorescent biotinylated HA crosslinked to surface labeled with FITC/Neutravadin. When not crosslinked, biotinylated HA washed away (4×). FIG. 2B is a glass slide for FIG. 2A. FIG. 2C is a SEM of the surface-modified film cross-sectional surface indicating pores filled, scale bar 2 µm and of a templated film, no surface modification, cross-sectional surface indicating unfilled porous, scale bar 1 µm, respectively.

Figure 3:
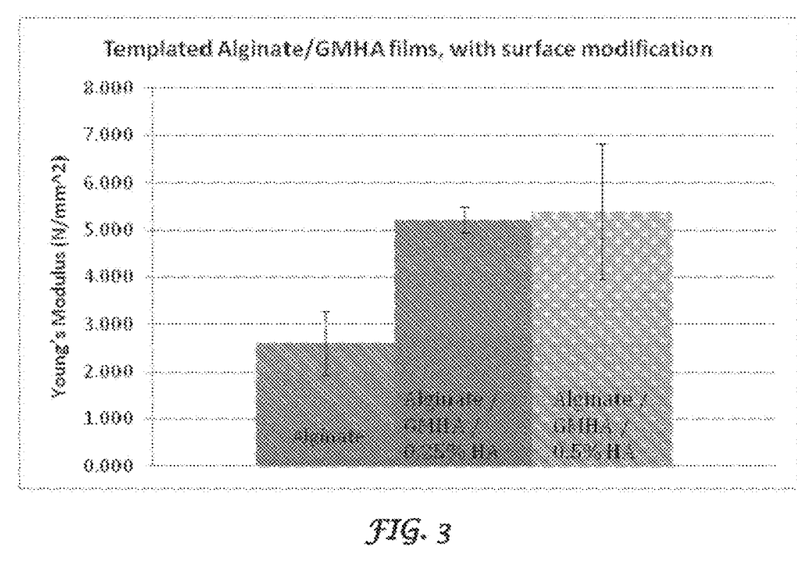
FIG. 3 is a plot showing the tensile strength (as measured by the Young's modulus) of Alginate/HA film patterned with an urea crystallization pattern.
Figure 4A:
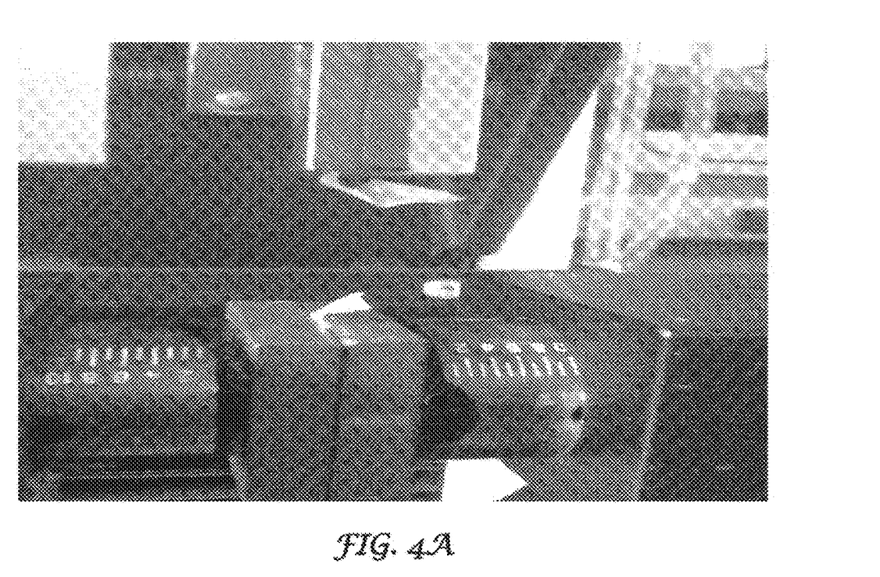
FIG. 4A urea patterned alginate/HA film and FIG. 4B alginate/HA film with no patterning.
Figure 4B:
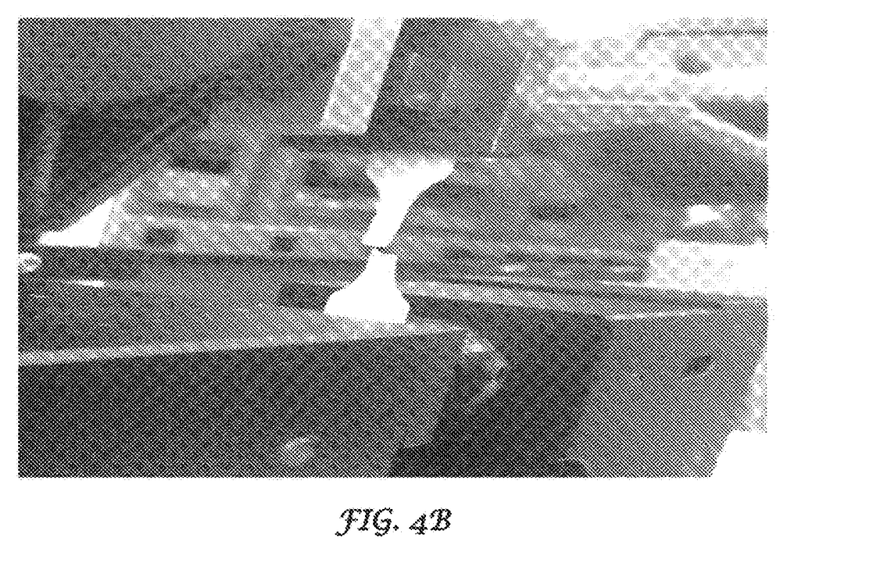
Figure 5A:
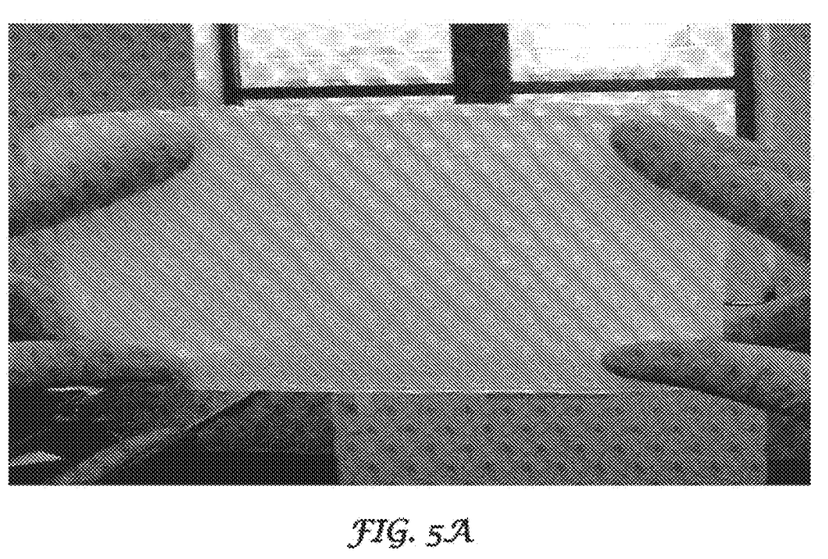
FIG. 5A linear patterning with 4% urea, 5" by 5" film, and FIG. 5B radial patterning with 6% urea, 3" by 3" film.
Figure 5B:
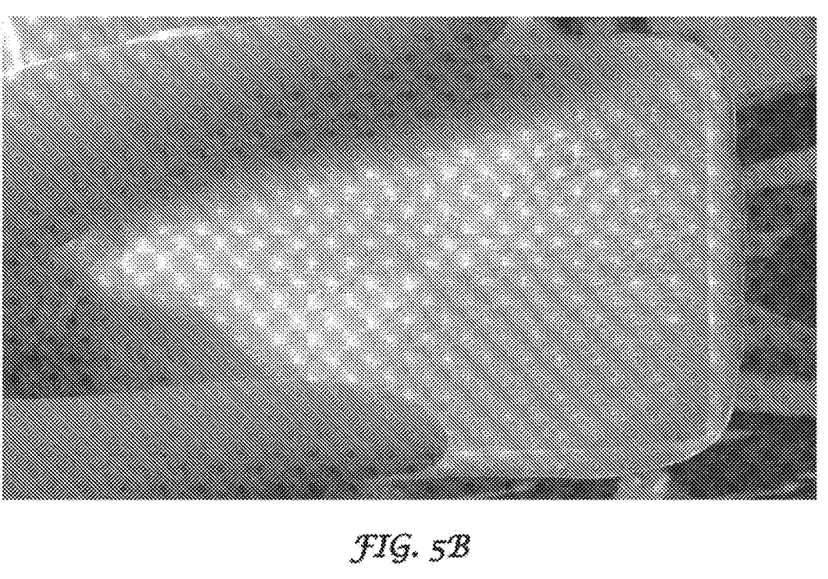
Figure 6:
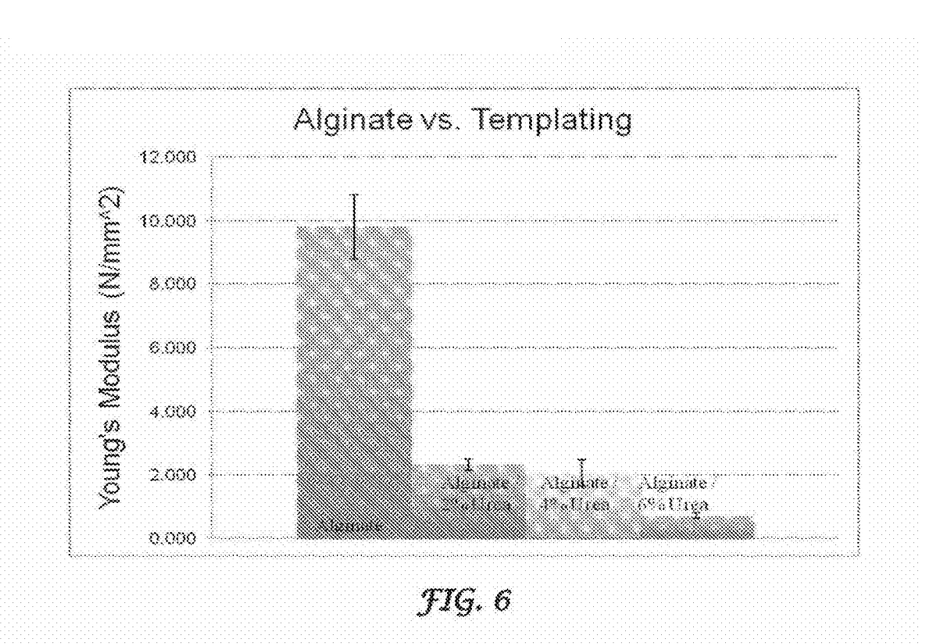
FIG. 6 is a plot showing the ASTM D638 tensile testing of alginate films with increased concentration of urea crystallization.

A plot showing the tensile strength (as measured by the Young's modulus) of Alginate/HA film patterned with an urea crystallization pattern is shown in FIG. 3. The modulus is significantly increased with surface modification and backfilling of HA. The films used were templated with 4% urea. The ASTM D638 tensile testing of urea patterned alginate/HA film and alginate/HA film with no patterning is shown in FIGS. 4A and 4B. The patterned film recoils in response to plastic deformation before failure. The non-patterned film breaks with a brittle fracture. Examples of alginate/HA urea-templated films are shown in FIGS. 5A and 5B, linear patterning with 4% urea, 5" by 5" film (FIG. 5A), and radial patterning with 6% urea, 3" by 3" film (FIG. 5B). FIG. 6 is a plot showing the ASTM D638 tensile testing of alginate films with increased concentration of urea crystallization. The trend indicates increased plasticity with increased crystallization patterning.

The instant invention provides significant advantages over existing methods. These include, (i) the resulting hydrogel(s) can be manipulated in a surgically relevant manner and, subsequently, return or retain original shape; (ii) this method works with biopolymers; (iii) the resulting hydrogel(s) can persist throughout the appropriate duration for given use; and (iv) the mechanical and/or chemical modulation may occur in one step.

It is contemplated that any embodiment discussed in this specification can be implemented with respect to any method, kit, reagent or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C or combinations thereof" is intended to include at least one of: A, B, C, AB, AC, BC or ABC, and if order is important in a particular context, also BA, CA, CB, CBA, BCA, ACB, BAC or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

WIPO Patent Publication No. WO 2009/107860 A8: Dendritic Macroporous Hydrogels Prepared by Crystal Templating.

What is claimed is:

1. An apparatus comprising:
   uncrosslinked hyaluronic acid included in a hydrogel; and
   crosslinked alginate included in the hydrogel;
   wherein (a) the alginate is crosslinked around the uncrosslinked hyaluronic acid, (b) the hyaluronic acid and the alginate are formed around a network of pores that are filled with a material; (c) the material includes at least one of additional hyaluronic acid, additional alginate, a drug, a growth factor, a hormone, a peptide, a protein, or combinations thereof.

2. The apparatus of claim 1, wherein the network is branched, the hydrogel includes a hydrogel film, and the alginate is crosslinked with calcium.

3. The apparatus of claim 1, wherein the material includes at least one of the additional hyaluronic acid or the additional alginate.

4. The apparatus of claim 1, wherein the material is chemically bonded to at least one of the hyaluronic acid or the alginate.

5. The apparatus of claim 1, wherein degradation rate of the hydrogel is tuned by at least one of addition or subtraction of the material to the network of pores.

6. The apparatus of claim 5, wherein mechanical properties of the hydrogel are tuned by at least one of addition or subtraction of the material to the network of pores, the mechanical properties selected from the group consisting of moduli, elasticity, tensile strength, or compression strength.

7. The apparatus of claim 1, wherein the hydrogel is configured to release the material when crosslinks included in the crosslinked alginate are disrupted.

8. The apparatus of claim 1, wherein the material includes at least one of the drug, the growth factor, the hormone, the protein, or combinations thereof.

9. The apparatus of claim 1, wherein the network is a crystal templated network.

10. The apparatus of claim 1, wherein the material is crosslinked to at least itself.

11. The apparatus of claim 1, wherein water has been at least partially removed from the hydrogel.

12. An apparatus comprising:
    uncrosslinked hyaluronic acid included in a hydrogel film; and
    crosslinked alginate included in the hydrogel film;
    wherein (a) the alginate is crosslinked around the uncrosslinked hyaluronic acid, (b) the hyaluronic acid and the alginate are formed around a network of pores that are filled with a material; and (c) the material includes at least one of additional hyaluronic acid or additional alginate.

13. The apparatus of claim 12, wherein the material is chemically bonded to at least one of the hyaluronic acid or the alginate.

14. The apparatus of claim 12, wherein degradation rate of the hydrogel film is tuned by at least one of addition or subtraction of the material.

15. The apparatus of claim 14, wherein (a) the alginate is crosslinked with calcium, (b) the material is backfilled into the pores, and (c) mechanical properties of the hydrogel film are tuned by at least one of addition and subtraction of the backfilled material, the mechanical properties selected from the group consisting of moduli, elasticity, tensile strength, or compression strength.

16. The apparatus of claim 12, wherein the hydrogel film includes at least one of a drug, growth factor, hormone, protein, or combinations thereof.

17. The apparatus of claim 16, wherein the hydrogel film is configured to release at least one of the drug, the growth factor, the hormone, the protein, or combinations thereof when crosslinks included in the crosslinked alginate are disrupted.

18. The apparatus of claim 12, wherein the material is crosslinked to at least itself.

19. The apparatus of claim 12, wherein water has been at least partially removed from the hydrogel film.

20. The apparatus of claim 12, wherein the material further includes at least one of a drug, a growth factor, a hormone, a peptide, a protein, or combinations thereof.

21. An apparatus comprising:
    uncrosslinked hyaluronic acid included in a hydrogel film; and
    crosslinked alginate included in the hydrogel film;
    wherein (a) the alginate is crosslinked around the uncrosslinked hyaluronic acid, (b) the hyaluronic acid and the alginate are formed around pores that are filled with a material; and (c) the material includes at least one of additional hyaluronic acid, additional alginate, a drug, a growth factor, a hormone, a peptide, a protein, or combinations thereof.

* * * * *